United States Patent
Nguyen (10) Patent No.: US 7,296,733 B2
(45) Date of Patent: Nov. 20, 2007

(54) DEVICE AND METHODS FOR STORING AND TRACKING PREGNANCY PROGRESS

(75) Inventor: Diep Mong Nguyen, Manhattan Beach, CA (US)

(73) Assignee: Voikex, Inc., Manhattan Beach, CA (US)

(*) Notice: Subject to any disclaimer, the term of this patent is extended or adjusted under 35 U.S.C. 154(b) by 0 days.

(21) Appl. No.: 11/340,075

(22) Filed: Jan. 25, 2006

(65) Prior Publication Data

US 2007/0102502 A1 May 10, 2007

Related U.S. Application Data

(63) Continuation-in-part of application No. 11/219,405, filed on Sep. 2, 2005.

(51) Int. Cl.
*G01G 23/18* (2006.01)
*G06M 1/06* (2006.01)
*G07G 1/00* (2006.01)

(52) U.S. Cl. ........................................ 235/1 R

(58) Field of Classification Search ............... 600/551, 600/511, 304, 300, 301, 587, 437, 441; 705/3; 715/835, 836; 235/1 R
See application file for complete search history.

(56) References Cited

U.S. PATENT DOCUMENTS

| | | | |
|---|---|---|---|
| 4,493,043 A | 1/1985 | Forbath | |
| 4,809,702 A | 3/1989 | Fabbri et al. | |
| 5,069,218 A | 12/1991 | Ikeda | |
| 5,213,108 A | 5/1993 | Bredesen et al. | |
| 5,265,613 A | 11/1993 | Feldman et al. | |
| 5,606,535 A | 2/1997 | Lynn | |
| 5,777,905 A | 7/1998 | Dowdle et al. | |

(Continued)

FOREIGN PATENT DOCUMENTS

GB 2193015 1/1988

(Continued)

OTHER PUBLICATIONS http://www.momstudy.com, "The Study of Maternal Observations and Memories of Stillbirth".

(Continued)

*Primary Examiner*—Max F. Hindenburg
*Assistant Examiner*—Brian Szmal
(74) *Attorney, Agent, or Firm*—Buchanan, Ingersoll & Rooney, LLP (57) ABSTRACT

Methods and a device for storing and tracking a pregnancy progress and for keeping up to a predetermined number of sound messages. The user of the device records sound messages, wherein the sound messages include a fetal heartbeat sound from a doctor's Doppler equipment, other personal messages from family or friends, and milestones (such as baby's first cry, first word, etc). The device includes a display screen that displays footprint icons, each of which corresponds to one of the sound messages stored in the device, whereby the user can count the number of sound messages by counting the icons. The display screen also displays an indication of pregnancy period from inception in weeks and days, and the countdown if the countdown is less than 100. During recording or playback of each sound message, the display screen sequentially displays the footprint icons to perform an animation.

21 Claims, 10 Drawing Sheets

U.S. PATENT DOCUMENTS

| | | | |
|---|---|---|---|
| 5,827,969 A | | 10/1998 | Lee et al. |
| 5,876,335 A | | 3/1999 | Handy et al. |
| 6,038,199 A | | 3/2000 | Pawlowski et al. |
| 6,045,500 A | | 4/2000 | Bieniarz |
| 6,083,156 A | | 7/2000 | Lisiecki et al. |
| 6,600,696 B1 | * | 7/2003 | Lynn ........................... 368/23 |
| 6,610,012 B2 | * | 8/2003 | Mault ......................... 600/437 |
| 7,034,691 B1 | * | 4/2006 | Rapaport et al. ........ 340/573.1 |
| 7,086,010 B1 | * | 8/2006 | Heiskari .................... 715/836 |
| 2003/0195775 A1 | * | 10/2003 | Hampton et al. .............. 705/3 |
| 2004/0076303 A1 | | 4/2004 | Vyshedskly et al. |
| 2005/0101841 A9 | * | 5/2005 | Kaylor et al. ............... 600/300 |
| 2005/0119585 A1 | | 6/2005 | Watrous |
| 2005/0177312 A1 | * | 8/2005 | Guerrant et al. ............. 702/19 |
| 2005/0267377 A1 | * | 12/2005 | Marossero et al. ......... 600/511 |
| 2006/0058650 A1 | * | 3/2006 | Sharony ..................... 600/437 |

FOREIGN PATENT DOCUMENTS

| | | |
|---|---|---|
| WO | WO 93/18710 | 9/1993 |
| WO | WO99/52020 | 10/1999 |
| WO | WO 2005/091249 A1 * | 9/2005 |

OTHER PUBLICATIONS

Thomas R. Moore, M.D., "A Prospective Evaluation of Fetal Movement Screening to Reduce the Incidence of Antepartum Fetal Death", *AM J Obstet Gynecol* 1989: 160:1075-80, May 1989.

Eliahu Sadovsky, M.D., "Fetal Movements in Utero—Nature, Assessment, Prognostic Value, Timing Delivery", *Dept. of Obstetrics and Gynecology at Hadassah University Hospital*, Jerusalem, Israel, vol. 50, No. 1, pp. 49-55, Jul. 1977.

Steen Neldam, "Fetal Movements as an Indicator of Fetal Wellbeing", *Dept. of Obstetrics and Gynaecology Y.B., Rigshospitalet, University Hospital*, Copenhagen, Denmark, *The Lancet*, pp. 1222-1224, Jun. 7, 1980.

James F. Pearson, "Fetal Activity and Fetal Wellbeing: an evaluation", *British Medical Journal*, pp. 1305-1307, May 29, 1976.

Philips Medical Systems: "*FM-2 Antepartum Portable Fetal Monitor*" 2004, XP002387584 Andover, Retrieved from Internet: URL. http://www.medical.philips.com/main/products/patient_monitoring/assets/docs/FM2_US_2004June.pdf [retrieved on Jun. 28, 2006].

* cited by examiner

DEVICE AND METHODS FOR STORING AND TRACKING PREGNANCY PROGRESS

CROSS REFERENCE TO RELATED APPLICATIONS

This application is a continuation-in-part of U.S. application Ser. No. 11/219,405, entitled "A device and methods for counting, timing, recording, and charting fetal movement frequency," and filed on Sep. 02, 2005.

FIELD OF THE INVENTION

The present invention relates to pregnancy progress monitoring, more particularly, to an electronic device for helping a relative/friend of a pregnant woman keep track of the pregnancy progress.

BACKGROUND OF THE INVENTION

In many cultures, child conception and birth is a time when the mother and her family come together to celebrate. Relatives/friends may offer their support, knowledge, wisdom, care, and practical help to the new mother. However, in the absence of traditional family support systems and postpartum support rituals, our society is witnessing a frightening rise in pregnancy related illnesses, such as antenatal and postpartum symptoms (www.radiantmother.com). Postpartum symptoms are a complex mix of emotional, physical and behavioral changes that are very treatable by skilled professionals. In spite of this, many women who suffer do not recognize there is something wrong, and only 1 in 5 will report their symptoms and receive help.

When new mothers are well informed, prepared and supported by family, friends, peers and professionals, they are less likely to experience overwhelming emotional distress during their pregnancy and postpartum months. Thus, there is a need for a simple, user friendly device that helps the new mother's family/friends track a pregnancy progress and provide support and an emotional bond during the pregnancy/postpartum period.

SUMMARY OF THE INVENTION

The present invention provides methods and a device for storing and tracking a pregnancy progress and for keeping up to a predetermined number of sound recordings. The user of the device records up to nine sound recordings, wherein the sound recordings include a fetal heartbeat sound from a doctor's Doppler equipment, other personal messages from family or friends, and milestones (such as baby's first cry, first word, etc). The device includes a display screen that displays footprint icons, each of which corresponds to one of the sound recordings stored in the device, whereby the user can count the number of sound recordings stored in the device by counting the icons displayed on the display screen. The display screen also displays the pregnancy period from inception in weeks and days, and the countdown if the countdown is less than a predetermined number. During recording or playback of each sound recording, the display screen sequentially displays the footprint icons to perform an animation.

In one aspect of the present invention, a device for tracking pregnancy progress includes: an input member actuatable by a user to record one or more sound recordings in the device; an audio member for playing back the sound recordings; and a display screen for displaying icons and pregnancy progress data, each icon corresponding to one of the sound recordings so that the user of the device is able to count the number of sound recordings recorded in the device by counting the icons.

In another aspect of the present invention, a method for tracking a pregnancy progress using a device that includes a display screen includes steps of: causing the device to record one or more sound recordings in the device; causing the device to display icons on the display screen, each of the icons corresponding to one of the sound recordings recorded in the device so that the user of the device is able to count the sound recordings by counting the icons; causing the device to play the sound recordings; and causing the device to sequentially display the icons during recording or playback of each of the sound recordings.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides a device that is intended to help the family of a pregnant woman store and track the pregnancy progress and keep up to a predetermined number of sound recordings. The user of the device may be able to record and play the fetal heartbeat sound from the doctor's Doppler equipment or other personal messages from family or friends or milestones (such as baby's first cry, first word, etc). Hereinafter, the terms sound recording and sound message are used interchangeably. The device may also store, update and display the weeks and days of the woman's pregnancy progress.

Figure 1A:
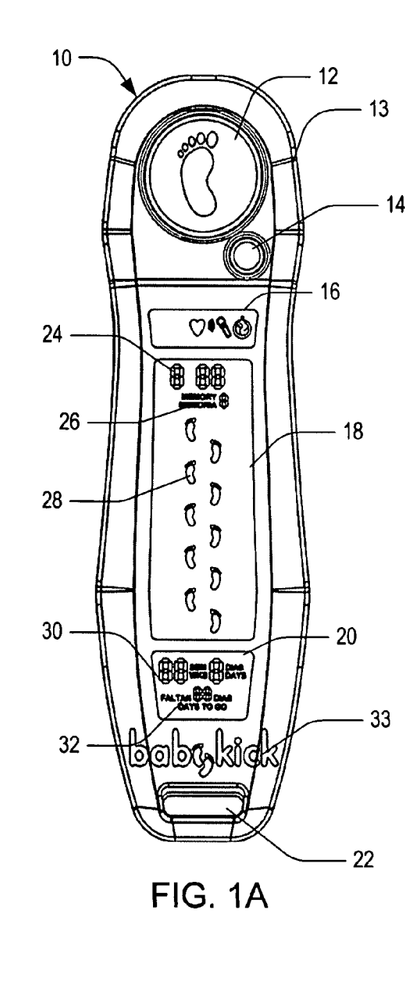
FIGS. 1A-1C are a front, a side and a back elevation of a device, respectively, in accordance with the present invention.

FIG. 1A is a front elevation of a kick-count device 10 in accordance with the present invention. As illustrated, the device 10 may include: an input member including an EVENT button 12 for recording events and a MODE button 14 for switching between modes; a mode window 16 for indicating the active mode; a record count window 18 that includes a time display 24, a memory number display 26, and a 10-footprint display 28; a pregnancy progress window 20 that includes a week-and-day counter 30 and a day counter 32. (Hereinafter, the terms footprints and foot icons are used interchangeably.) The time display 24 may display two numbers in the units of second and one hundredth of a second, respectively. The week-and-day counter 30 may indicate a count forward of the pregnancy in weeks and days from the inception of pregnancy, while the day counter 32 may indicate a countdown of 'days-to-go' during the last 99 days of the pregnancy. As will be explained later, the words "DAYS TO GO" of the day counter 32 may also be used to select the language by the user of the device 10. The device 10 may have one LCD screen that is masked by a front enclosure 13 to be perceived as three separate windows 16, 18 and 20. The LCD screen may be also used to display a digital image of the baby's ultrasound scan. Alternatively, a printout of the digital image may be slotted into a clear plastic pouch, where the pouch is attached to the front enclosure 13 or the back enclosure 15 (FIG. 1B).

The device 10 may also have a hole 22 through the enclosure to attach a strap for a key ring, wrist strap, necklace or the like. In an alternative embodiment, the device 10 may have a clip feature (not shown in FIG. 1A) so that it can be attached to a belt, clothing or a bag.

The website address 37 (shown in FIG. 1C), Voikex™ logo 35 (shown in FIG. 1C) and device name 33 may be located on the device 10. These graphics may be added as a part of the molding process or printed onto the device 10. The EVENT button 12 may be concave and level with the enclosure at the edges. The EVENT button 12 may be made of an elastomeric material, while the MODE button 14 may be made of a rigid plastic. In another alternative embodiment, the EVENT button 12 may be located at the top the device 10.

Figure 1B:
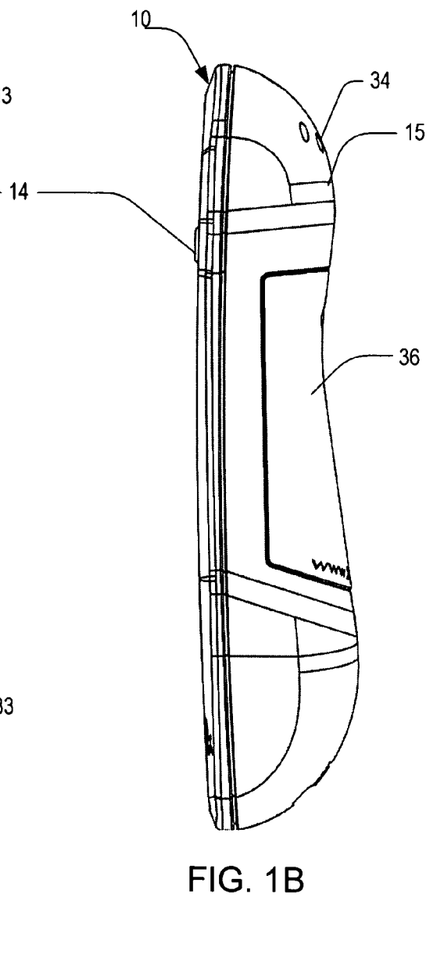

FIG. 1B is a side elevation of the kick-count device 10 depicted in FIG. 1A. As illustrated, the device 10 may include a back enclosure 15 that may be fixed to the front enclosure 13 securely and may not snap open when subjected to predictable impacts. The back enclosures 15 may include a removable battery cover 36 and holes 34 for a speaker located therewithin. The speaker, not shown in FIGS. 1A-1C, may be used to record a recognizable sound, such as fetal heartbeat sound from a Doppler heartbeat audio instrument, and play the recorded sound. Further detail of the speaker will be given in connection with FIG. 3. The front and back enclosure 13 and 15 may have a pregnancy totem shape reminiscent of pregnant abdomen with a gentle female curvature.

Figure 1C:
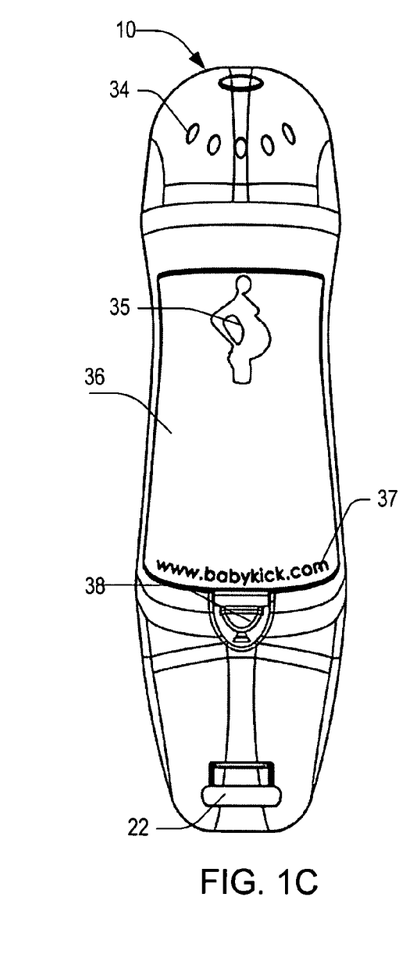

FIG. 1C is a back elevation of the kick-count device 10 depicted in FIG. 1A. As illustrated, the back enclosure 15 may include: holes 34 for the speaker; a removable battery cover 36; and a battery cover opener 38 that opens the removable battery cover 36.

Figure 2A:
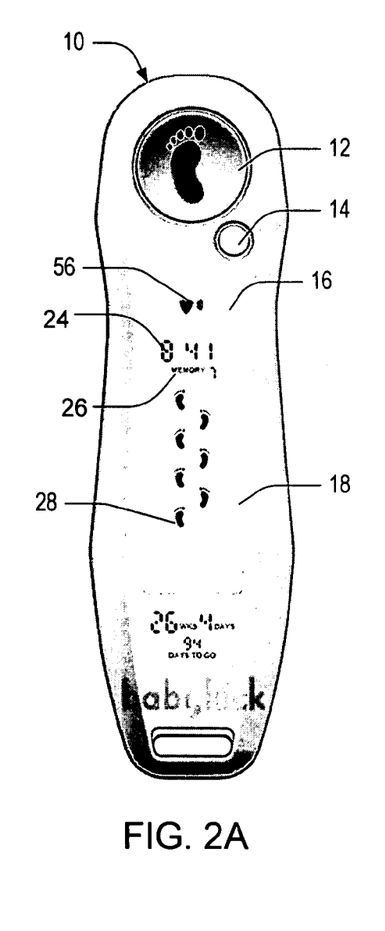
FIG. 2A is an exemplary display on the device of FIG. 1A in a "play" mode.

The device 10 may have the following (operational) modes; play mode, record mode and setup mode. The device may include audible instructions for each mode that will play after a predetermined time delay. These instructions may inform the user in the correct language how to operate the device in that particular mode. The user of the device 10 may press the MODE button 14 to switch from one mode to another while one of the icons in the mode window 16 may be highlighted to indicate the current mode. FIG. 2A is an exemplary display on the device 10 in a "play" mode for exhibiting the information of recorded sounds. The device 10 may default to the play mode when awaken from an idle state or after a period of inactivity in another mode. As illustrated, a play icon 56 may be highlighted in the mode window 16 to indicate that the device 10 is currently operating in the play mode. In this mode, the record count window 18 may display indications of up to nine sound recordings stored in the device 10. Each recording position may be represented on the screen 18 with a footprint (or, equivalently, foot icon) 28, wherein each foot icon 28 may indicate a recorded message of sound. Each sound may be a fetal heartbeat sound from the doctor's Doppler equipment or other personal messages from family or friends or milestones (such as baby's first cry, first word, etc), and may be up to ten seconds long. It is noted that the present invention may be practiced with other suitable number and length of sound recordings.

Figures 2B, 2C:
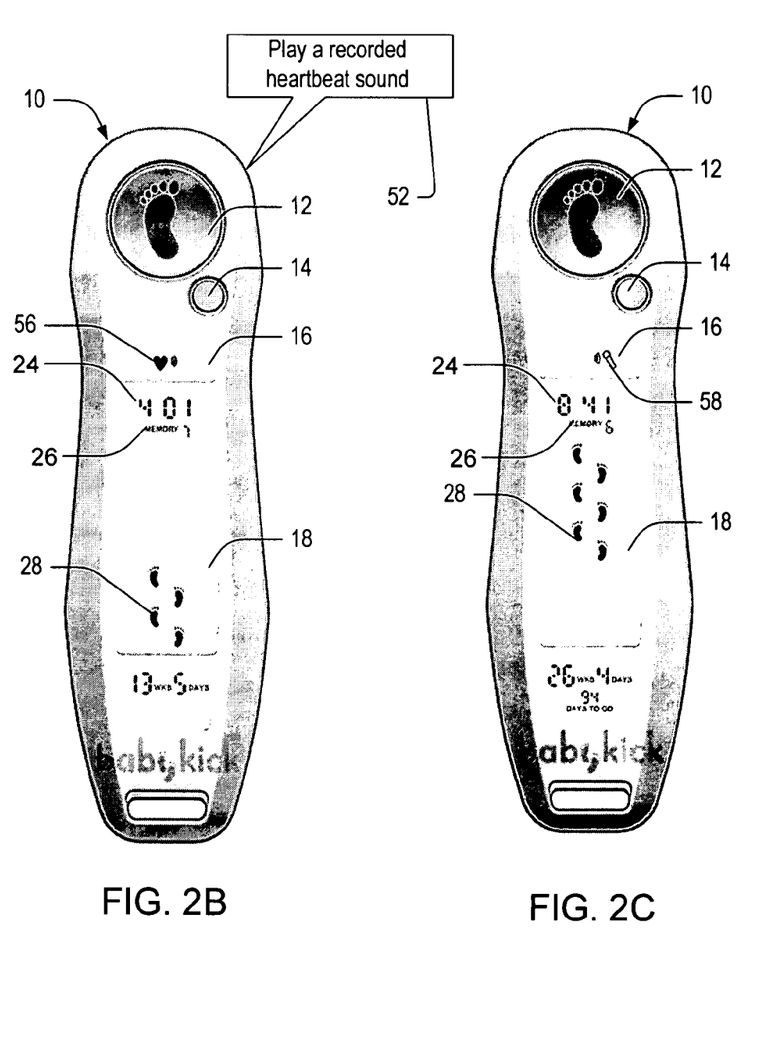
FIG. 2B is an exemplary display on the device of FIG. 1A during playback of a sound recorded therein.
FIG. 2C is an exemplary display on the device of FIG. 1A in a "record" mode.

The user may press the EVENT button 12 to scroll down through the sound recordings. To help the user trace the sound record number, the corresponding footprint will be highlighted in the record count window 18 each time the user pushes the EVENT button 12. Also, the record number may be displayed on the memory number display 26. The time display 24 window may indicate the length of the corresponding sound. In the play mode, when the user presses and holds the EVENT button 12 more than a preset time interval, say ½ second, the device 10 may play the sound recording that corresponds to the selected footprint, as illustrated in FIG. 2B. FIG. 2B shows an exemplary display on the device 10 during playback of a sound recording. When the device 10 plays a sound recording, the play icon 56 may blink and the animated footprints 28 may walk up the record count window 18. The time display 24 may represent the time elapsed since the playback has started. In the preferred embodiment of the present invention, up to ten footprints may be sequentially displayed to perform the animation for up to ten seconds. The user may press the MODE button 14 to exit the play mode and switch to a "record" mode.

FIG. 2C shows an exemplary display on the device 10 in the record mode for exhibiting the information of audio sounds to be played in the play mode. As illustrated, a record icon 58 may be displayed on the mode window 16 to indicate that the device 10 is currently operating in the record mode. In this mode, the record count window 18 may display indications of up to nine sound recordings stored in the device 10. Each recording position may be represented on the screen 18 with a footprint 28, wherein each footprint 28 may indicate a recorded message of sound. In the record mode, the user may press the EVENT button 12 to scroll down through the sound recordings. A footprint corresponding to the selected sound recording will be highlighted on the screen each time the user presses the EVENT button 12. To help the user trace the sound record number, the record number for each sound recording may be shown on the memory number display 26, as illustrated in FIG. 2C. In addition, the time display 24 may indicate the length of the sound recording.

A blinking footprint may indicate an empty message location that is ready to record a sound message. When entering the record mode, the next empty recording slot may automatically be selected (and blinking). When nine messages have been recorded, the record number 9 may be the default for the next recording. The user may bring the device 10 to an obstetrical provider and record the fetal heartbeat sound from a Doppler instrument by pressing and holding the EVENT button 12 more than a preset time interval, say ½ second. The user may also record other messages by pressing and holding the EVENT button 12 more than a preset time interval and providing a sound message for the microphone contained in the device 10.

Figure 2D:
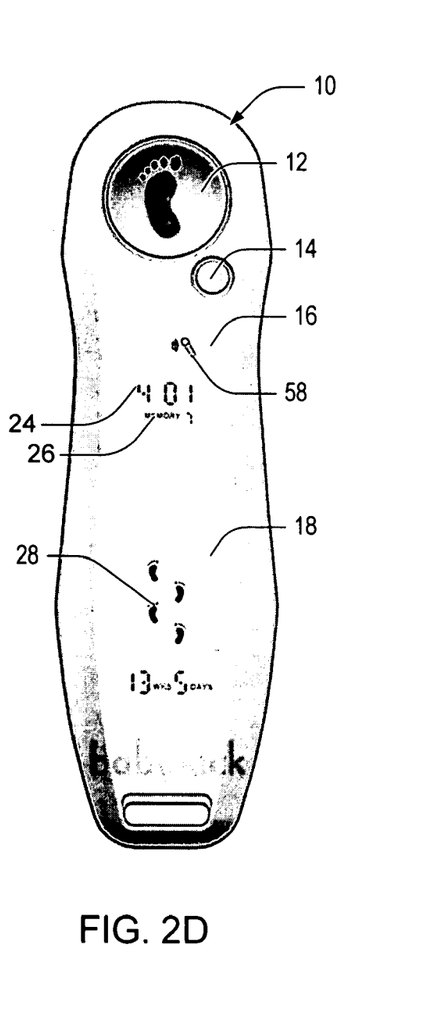
FIG. 2D is an exemplary display on the device of FIG. 1A during recording of a sound.

FIG. 2D shows an exemplary display on the device 10 during recording of a sound. The record icon 58 may flash for up to 10 seconds from the start of recording and subsequently stay highlighted to indicate that the recording has completed. Also, the animated footprints 28 may walk up the record count window 18 during the recording. The time display 24 may indicate the time elapsed since the recording has started. For example, the numbers on the time window 24 and memory number display 26 of FIG. 2D indicate that the user has been recording for 4.01 seconds in the record memory number 7.

To select a message for overwriting, the user may select the message in the record mode by using the EVENT button 12 to scroll down to the required location. The user may then record a message by pressing and holding the EVENT button 12, which may overwrite the old message.

To delete a sound recording, the user may select the message in the play mode by using the EVENT button 12 to scroll down to the required location. The user may then press both EVENT button 12 and MODE button 14 at the same time. This will cause the sound recording to be erased. The footprint that previously indicated a sound recording in that location will disappear until a new recording is made in that location.

Figure 2E:
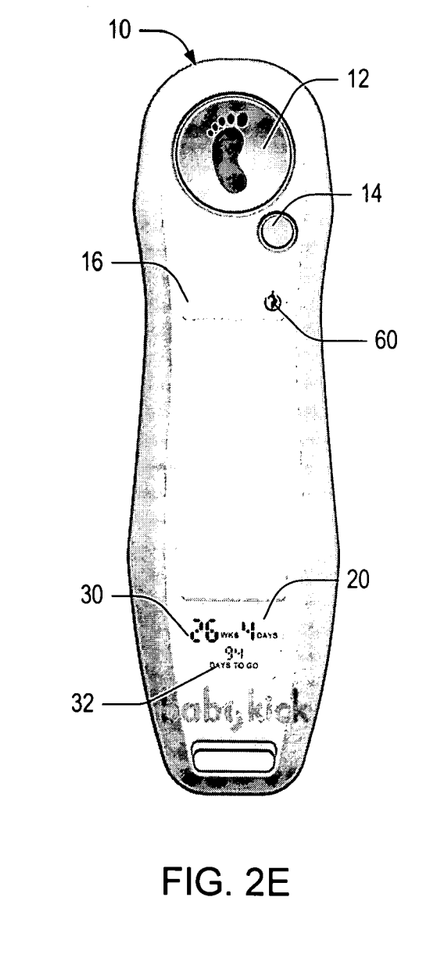
FIG. 2E is an exemplary display on the device of FIG. 1A in a "setup" mode for inputting information of the current stage of pregnancy and selecting a language. The "Days To Go" countdown will update based on the current stage of pregnancy.

The user may press and hold the MODE button 14 to exit the record mode and switch to a "setup" mode. FIGS. 2E shows an exemplary display on the device 10 in the setup mode for inputting information of the current stage of pregnancy into the device 10. The setup mode has three submodes: "SetWeeks", "SetDays" and "SetLanguage" submodes. When the device 10 enters the SetWeeks submode, the number representing the "Weeks Pregnant" in the week-and-day counter 30 may flash indicating that the device 10 is operating in the SetWeeks submode. The user may press the EVENT button 12 to set the weeks, where the weeks may loop from 0 to 42 and back to 0. To switch from the SetWeeks submode to the SetDays submode, the user may press the MODE button 14 to accept the value entered for the "Weeks Pregnant." In the SetDays submode, the number representing the "Days Pregnant" (in addition to the weeks pregnant) in the week-and-day counter 30 may flash and the user may press the EVENT button 12 to set the days, wherein the days may loop from 0 to 6.

The device 10 may be set to count forward from the inception of pregnancy as well as to count down until the completion of 40 weeks of pregnancy. If the user's input for the week-and-day counter 30 indicates that the current date is in the last 99 days of the pregnancy, the device 10 may additionally display the count-down days on the day counter 32 as illustrated in FIG. 2E.

To switch from the SetDays submode to the SetLanguage submode, the user may press the MODE button 14 to accept the value entered for the "Days Pregnant." The words "DAYS TO GO" or "FALTAN_DIAS" of the day counter 32 may blink to indicate the currently selected language. The user may toggle between the languages by pressing the EVENT button 12 and select one by pressing the MODE button 14. Once a language is selected, the graphics on the windows 16, 18 and 20 may be displayed in the selected language. To exit the "setup" mode, the user may press and hold the MODE button 14 in the same way as to enter the "setup" mode.

When a new battery(ies) are installed in the device 10, the device may enter the SetLanguage submode prompting the user to select a language. After setting the language, the "Days Pregnant" and the "Weeks Pregnant," the user may exit the setup mode by pressing the MODE button 14. It should be apparent to those of ordinary skill that the device 10 may be designed to display languages other than English and Spanish. Also, the ordinary skill in the art would appreciate that the design engineer of the device 10 can easily change the shapes of the icons displayed on the display windows 16 and 18. The device may have an alert to inform the user that the battery power is running low. This alert may be in the form of a visible indicator on the screen or an audio warning.

Figure 3:
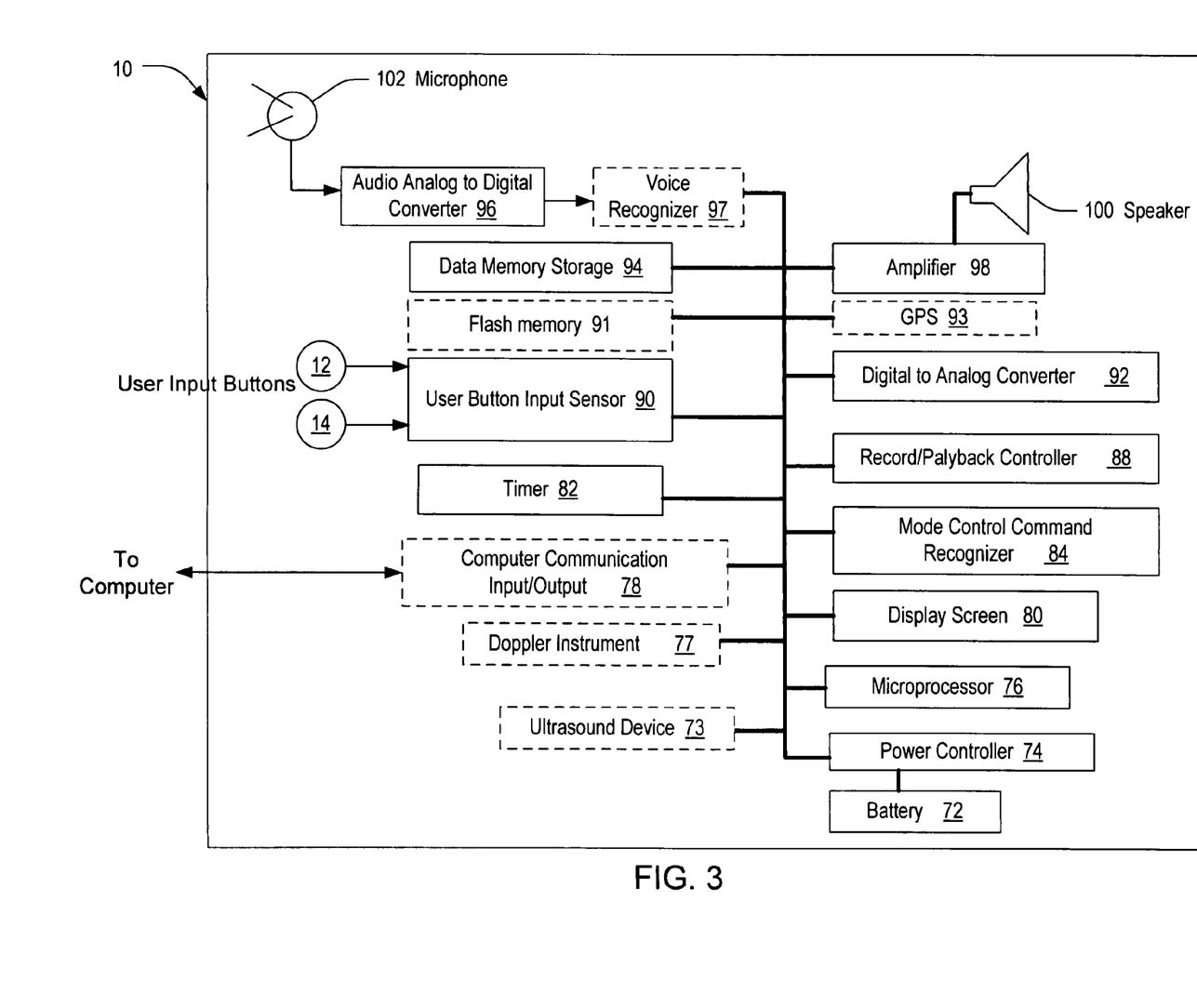
FIG. 3 is a functional block diagram of the device depicted in FIG. 1A.

FIG. 3 is a functional block diagram of the device 10. The device 10 may include: a microphone 102 for receiving audio messages or fetal heartbeat sound from a Doppler instrument in the record mode; an analogue-to-digital converter 96 for converting the sound input received from the microphone 102 into a digital signal; a data memory storage (or, shortly, data storage) 94 for storing the converted digital signal; a digital-to-analogue converter 92 for converting the stored digital signal into an analogue signal; an amplifier 98 for amplifying the analogue signal received from the digital-to-analogue converter 92; a speaker 100 for playing the amplified analogue signal received from the amplifier 98; two buttons (EVENT and MODE buttons 12, 14); a user button input sensor 90 for receiving the user's input through the two buttons 12 and 14; a timer 82 for timing events, such as internal clock timing; a record/playback controller 88 for controlling the length of a recorded sound and adjusting the volume of the speaker 100; a mode control command recognizer 84 for receiving signals from the user button input sensor 90 and determining the current operational mode; a display screen 80, preferably a LCD screen, masked by the front enclosure 13 to appear as three separate windows 16, 18 and 20; a power controller 74 for receiving power from a battery(ies) 72 and switching to sleep mode when the device 10 is in the idle state; and a microprocessor 76 for controlling and orchestrating the elements of the device 10 shown in FIG. 3. (Hereinafter, the term "audio member" may collectively refer to the speaker 100 and the microphone 102.) It is noted that the speaker 100 may be also used as a microphone and record other suitable sounds, such as a baby's first cry or words, as well as the fetal heartbeat sound. In an alternative embodiment, a solar panel may be used in place of the battery 72.

The data (memory) storage 94 may also store other information including names, obstetrical data such as fetal development milestones, personal medical and emergency information, medical visits, gestational age specific recommendation, organizer, calendar, chronometer and pediatric data, such as pediatric growth chart. Each of the sound recordings stored in the data (memory) storage 94 may include a tag for the time of the recording.

Optionally, the device 10 may include one or more of the followings: a computer communication Input/Output 78 for exchanging information, such as the sound messages recorded in the device 10, with a computer; a voice recognizer 97 for recognizing the user's voice to understand verbal commands and activating the device 10 in accordance with the commands; a built-in Doppler instrument 77 for picking up fetal heartbeat sound and playing/recording the sound; a built-in ultrasound device 73 for sensing and/or imaging fetal movement, the image being displayed on the display screen 80; a flash memory 91 for storing verbal instructions for use of the device 10; and a global positioning system (GPS) 93 for determining the user's current location and providing a navigational guidance to a destination, such as a hospital, for the user. In an alternative embodiment, the flash memory 91 may be included in the data memory storage 94.

It will be appreciated by those of the ordinary skill that elements illustrated in FIG. 3 may be modified in a variety of ways without departing from the spirit and scope of the present invention. For example, the mode control command recognizer 84 may be a firmware or software stored in the data memory storage 94 and executed by the microprocessor 76. In another example, the computer communication Input/Output 78 may be configured to communicate with various electronic devices, such as PDA or other suitable hand-held devices, as well as a computer.

The device 10 may use a conventional wireless/blue tooth technology to connect to a computer to upload or download the data stored in storage 94. The device 10 may also incorporate an MP3, writing instrument, compact mirror, watch, clock, pendant, bracelet, key chain and software for PDA or PC.

Figure 4A:
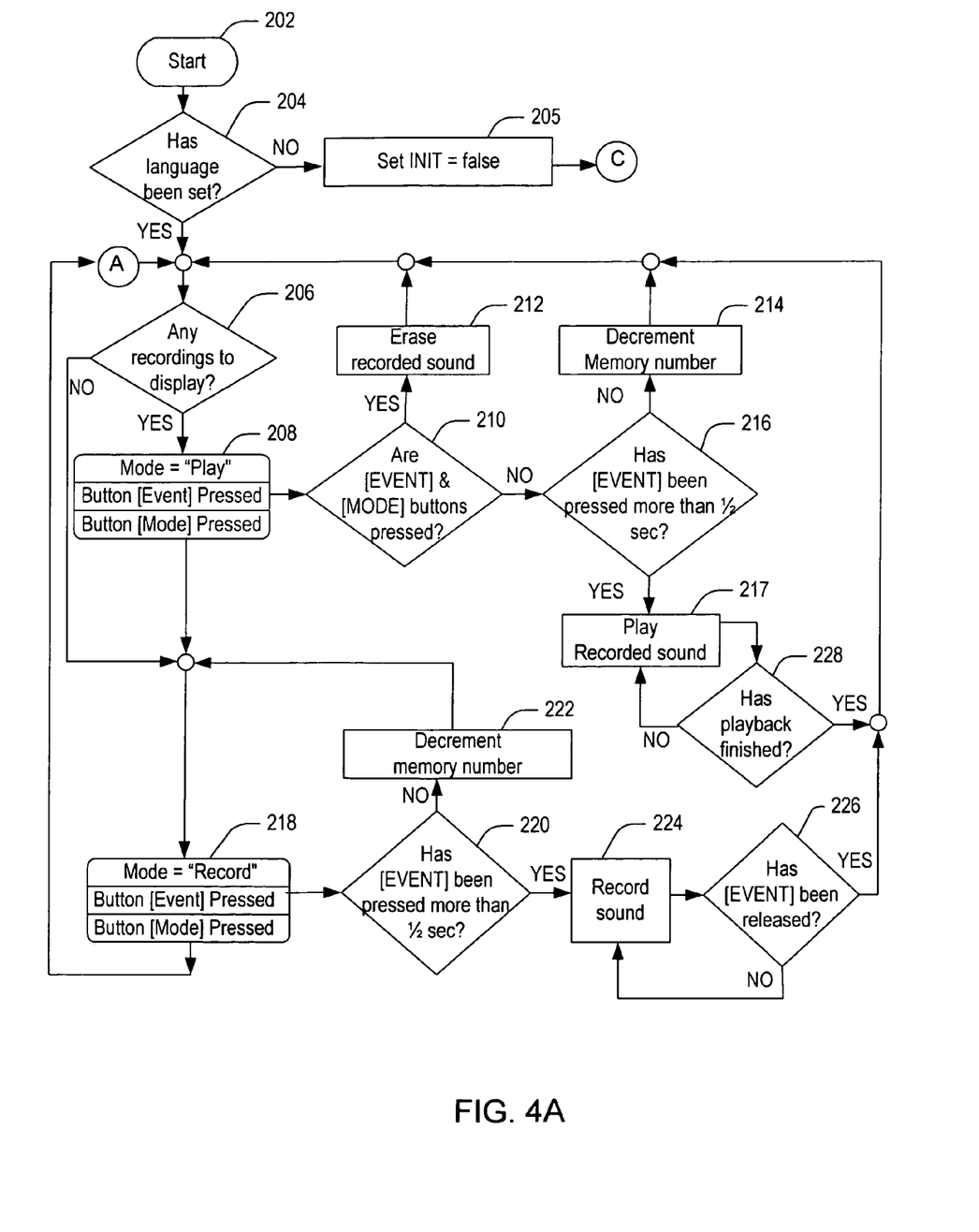
FIGS. 4A-4B show a flow chart illustrating an operational sequence of the modes depicted in connection with FIGS. 2A-2E.
Figure 4B:
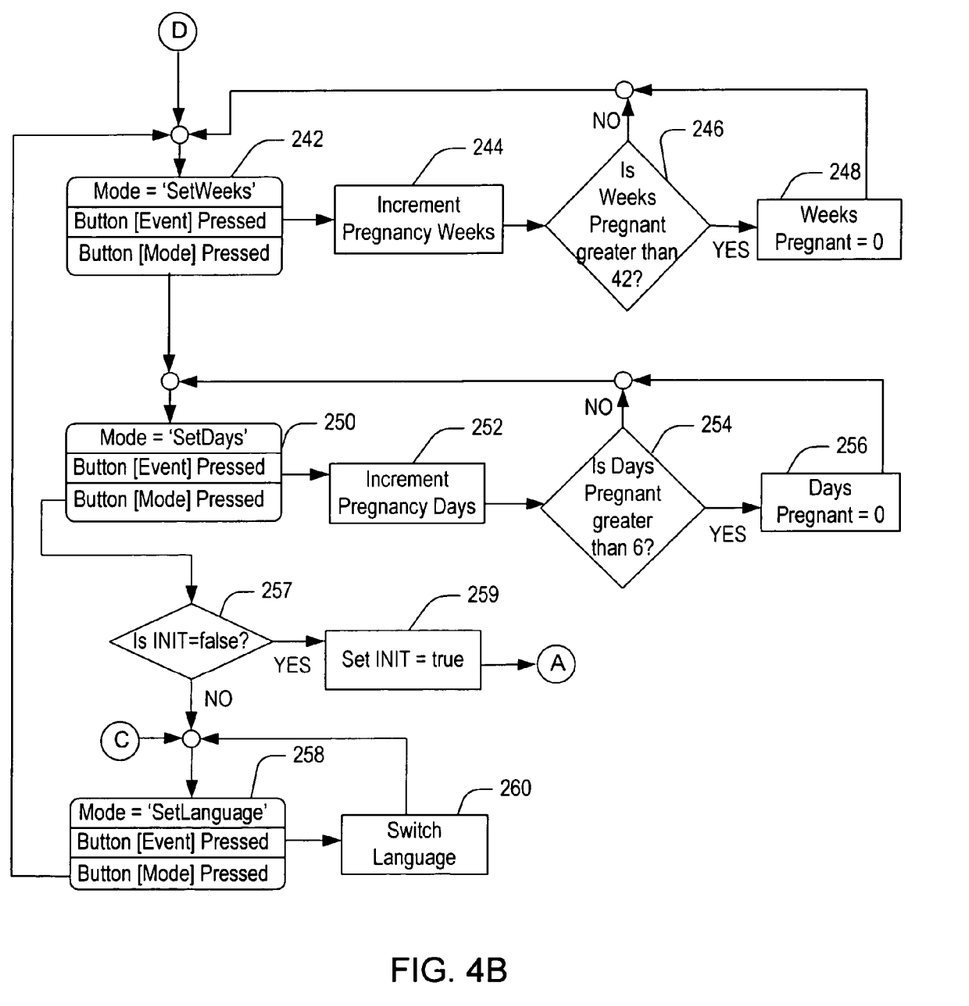

FIGS. 4A-4B show a flow chart illustrating the operational sequence of the modes depicted in connection with FIGS. 2A-2E. The process may start in a state 202. Next, in a state 204, the device 10 may check if the user has selected a language. Upon negative answer to the state 204, a variable, 'INIT', may be set to false in a state 205. Then, the process may advance to a state 258 (shown and illustrated in connection with FIG. 4B). Otherwise, the user may press the MODE button 14 to proceed to a state 206.

In the state 206, the decision is made as to whether the data memory storage 94 (FIG. 3) has any sound recording to play. Upon negative answer to the state 206, the process may proceed to a state 218. Otherwise, the process may proceed to a state 208.

The state 208 may correspond to the play mode. In the state 208, the user may press the EVENT button 12, causing the process to proceed to a state 210. In the state 210, the decision is made as to whether the MODE and EVENT buttons have both been pressed. Upon positive answer to the state 210, the process may proceed to a state 212. In the state 212, the recording at the selected memory location may be deleted. Then, the process may proceed to the state 206. If the answer to the state 210 is negative, the process may proceed to a state 216. In the state 216, it is determined whether the EVENT button 12 has been pressed more than ½ second. Upon negative answer to the state 216, the process may proceed to the state 214. In the state 214, the selected memory number is decreased. Then, the process may proceed to the state 206. If the answer to the state 216 is YES, the process may proceed to a state 217. In the state 217, the record/playback controller 88 (FIG. 3) may play the recorded sound. Next, in a state 228, the record/playback controller 88 may determine whether the playback has completed. Upon positive answer to the state 228, the process may advance to the state 206. If the answer to the state 228 is NO, the process may proceed to the state 217.

If the user presses the MODE button in the state 208, or if the answer to the state 206 is negative, the process may proceed to a state 218. The state 218 may correspond to the record mode. In the state 218, the user may press the EVENT button 12, causing the process to proceed to a state 220. In the state 220, a determination is made as to whether the EVENT button 12 has been pressed more than ½ second. Upon negative answer to the state 220, the process may proceed to a state 222. In the state 222, the selected memory number may be decreased. Then, the process may proceed to the state 218. If the answer to the state 220 is YES, the record/playback controller 88 (FIG. 3) may record the sound by pressing and holding the EVENT button 12 in a state 224. Next, in a state 226, the record/playback controller 88 may determine whether the EVENT button 12 has been released. Upon positive answer to the state 226, the process may advance to the state 206. If the answer to the state 226 is NO, the process may proceed to the state 224.

If user presses the MODE button 14 in the state 218, the process may proceed to a state 206. If the MODE button 14 is pressed and held for more than 2 seconds at any point in the flowchart shown in FIG. 4A, the device will proceed to state 242 in FIG. 4B.

In FIG. 4B, the state 242 may correspond to the SetWeeks submode. In the state 242, the user may press the EVENT button 12 causing the process to proceed to a state 244. In the state 244, the device 10 may increase the Weeks Pregnant (or, equivalently, Pregnancy Weeks) in the week-and-day counter 30 by one each time the user presses the EVENT button 12. Next, in a state 246, a determination may be made as to whether the Weeks Pregnant is greater than 42. Upon negative answer to the state 246, the process may proceed to the state 242. Otherwise, the process may advance to a state 248. In the state 248, the Weeks Pregnant may be set to zero. Then, the process may proceed to the state 242.

If the user presses the MODE button 14 in the state 242 to accept the value entered for "Weeks Pregnant," the process may proceed to a state 250. The state 250 may correspond to the SetDays submode. In the state 250, the user may press the EVENT button 12 causing the process to proceed to a state 252. In the state 252, the device 10 may increase the Days Pregnant (or, equivalently Pregnancy Days) in the week-and-day counter 30 by one each time the user presses the EVENT button 12. Next, in a state 254, a determination may be made as to whether the DueDays is greater than 6. Upon negative answer to the state 254, the process may proceed to the state 250. Otherwise, the process may advance to a state 256. In the state 256, the Days Pregnant may be set to zero. Then, the process may proceed to the state 250.

If the user presses the MODE button 14 in the state 250 to accept the value entered for "Days Pregnant", the process will check the state of the variable, 'INIT', in a state 257. If the variable INIT is false, then the variable is set to true in a state 259 and the process may advance to state 206 in FIG. 4A. Otherwise the process may proceed to a state 258. The state 258 may correspond to the SetLanguage submode. In the state 258, the user may press the EVENT button 12 causing the process to proceed to a state 260. In the state 260, the user may select a language as described in connection with FIG. 2C. Then, the process may advance to the state 258. The user may press the MODE button 14 in the state 258, causing the process to proceed to the state 242.

Figure 5A:
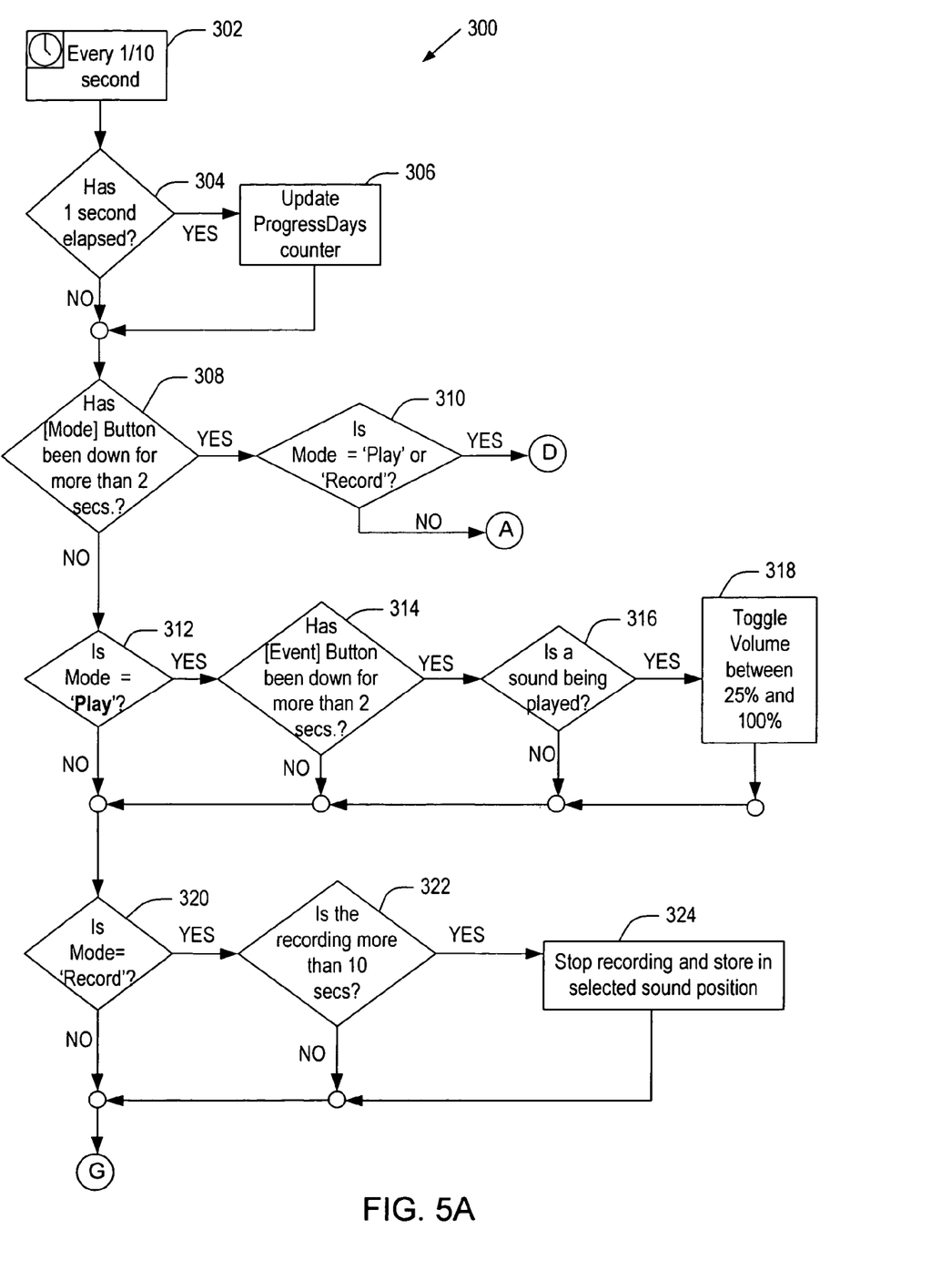
FIGS. 5A-5C show a system flowchart of the device depicted in FIG. 1A.
Figure 5B:
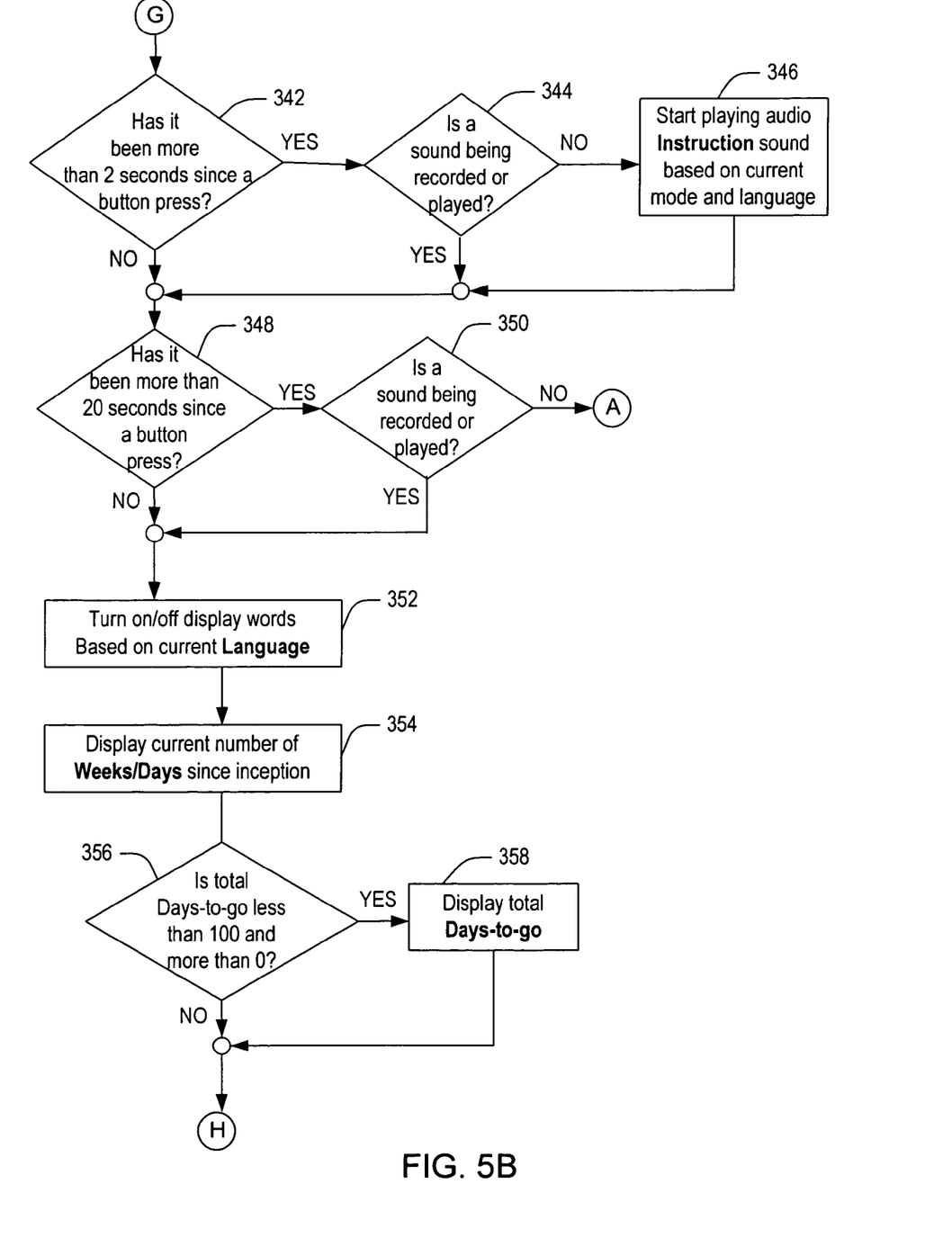
Figure 5C:
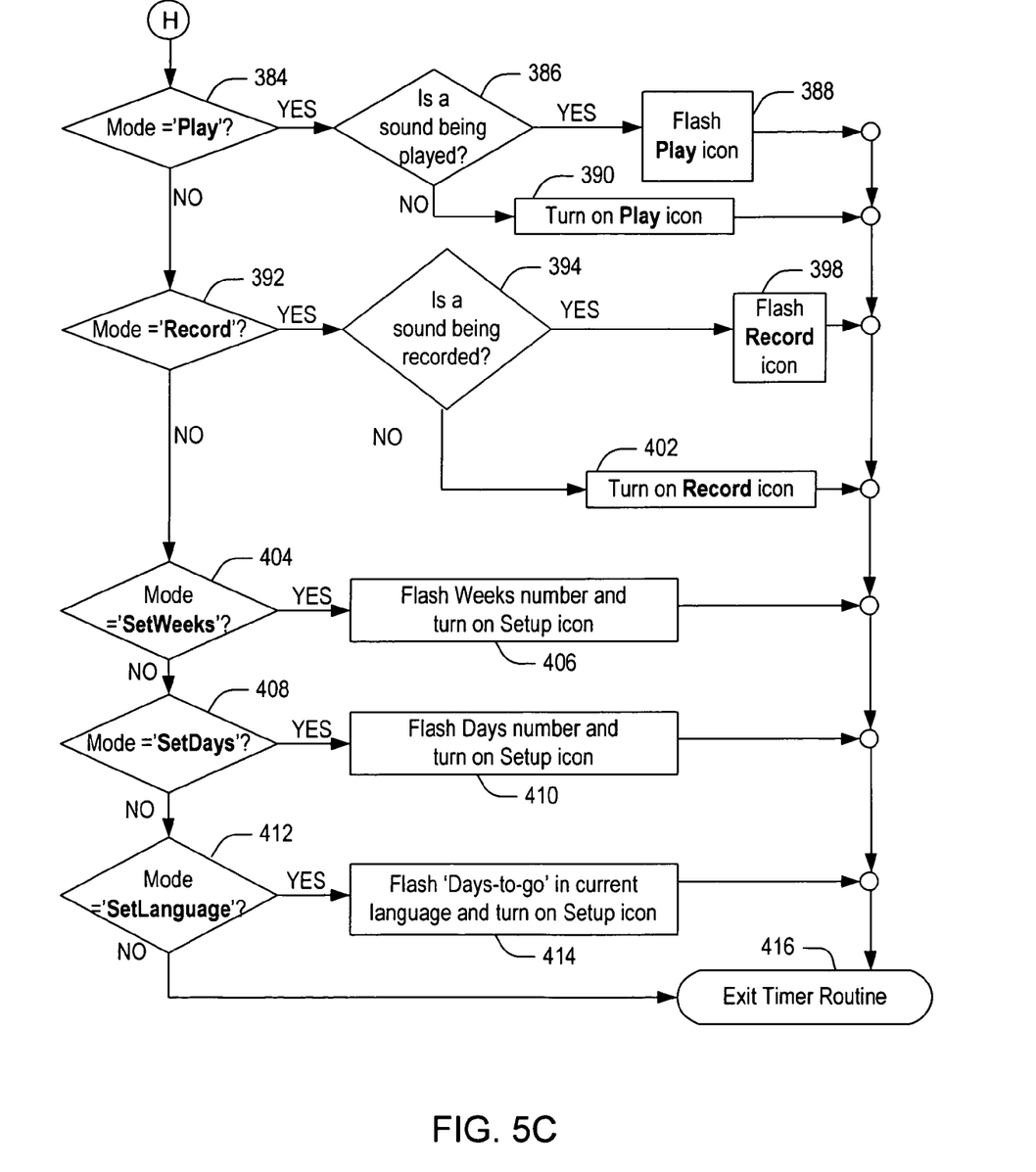

FIGS. 5A-5C show a system flowchart shown at 300 of the device 10. The process may start at every ⅒ second in a state 302, where the timer 82 (FIG. 3) may provide the clock time. Next, the process may advance to a state 304, where a determination may be made as to whether one second has elapsed. Upon positive answer to the state 304, the progress may advance to a state 306. In the state 306, the device 10 may update the ProgressDays counter, where the ProgressDays collectively refer to the "Weeks and Days Pregnant" of the week-and-day counter 30 and the countdown of days-to-go of the day counter 32. Then, the process may advance to a state 308. If the answer to the state 304 is negative, the process may also proceed to the state 308.

In the state 308, a decision may be made as to whether the MODE button 14 has been held down for more than 2 seconds. Upon positive answer to the state 308, the process may proceed to a state 310. In the state 310, a decision may be made as to whether the current mode is either the play or record mode. Upon positive answer to the state 310, the process may proceed to a state 242 in FIG. 4B. Upon negative answer to the state 310, the process may proceed to a state 206 in FIG. 4A. Upon negative answer to the state 308, the process may proceed to a state 312.

In the state 312, a decision may be made as to whether the current mode is the play mode. Upon positive answer to the state 312, the process may proceed to a state 314. In the state 314, the user button input sensor 90 may determine if the user has pressed down the EVENT button 12 for more than 2 seconds. If the answer to the state 314 is YES, the process may proceed to a state 316. In the state 316, a determination may be made as to whether the sound is being played. If the sound is being played, the speaker volume may toggle between 25% and 100% of the maximum level in a state 318. Then, the process may proceed to the state 320. Upon negative answer to the states 312 or 314 or 316, the process may also proceed to the state 320.

In the state 320, a decision may be made as to whether the current mode is the record mode. Upon positive answer to the state 320, the process may proceed to a state 322. In the state 322, a determination may be made as to whether the recording is more than 10 seconds. If the answer to the state 322 is YES, the process may proceed to a state 324 to stop recording. Subsequently, the process may proceed to the state 342 in FIG. 5B. If the answer to the state 320 is negative or the answer to the state 322 is negative, the process may also proceed to the state 342.

In the state 342, the user button input sensor 90 (FIG. 3) may determine whether more than 2 seconds has elapsed since any button has been pressed. If the answer to the state 342 is YES, the process may proceed to a state 344. In the state 344, a determination may be made as to whether a sound is being recorded or played. If the answer to the state 344 is NO, the process may proceed to a state 346. In the state 346, the record/playback controller 88 may start playing audio instruction sound based on the current mode and language. Then, the process may proceed to a state 348. If the answer to the state 342 is NO or the answer to the state 344 is YES, the process may also proceed to the state 348.

In the state 348, the user button input sensor 90 (FIG. 3) may determine if more than 20 seconds has elapsed since a button has been pressed. If the answer to the state 348 is YES, the process may proceed to a state 350. In the state 350, a determination is made whether a sound is being recorded or played. If the answer to the state 350 is NO, the process may proceed to a state 206 in FIG. 4A. If the answer to the state 350 is YES or the answer to the state 348 is NO, the process may advance to a state 352.

In the state 352, the display screen 80 may turn on/off the displayed words based on the current language. Next, in a state 354, numbers of weeks and days may be displayed on the week-and-day counter 30. Subsequently, the process may proceed to a state 356.

In the state 356, a determination is made whether the countdown days-to-go is less than 100 and more than 0. If the answer to the state 356 is YES, the process may proceed to a state 358 to display the countdown 'DAYS TO GO' on the day counter 32. Then, the process may proceed to a state 384 (FIG. 5C). If the answer to the state 356 is NO, the process may also proceed to the state 384.

As depicted in FIG. 5C, a determination is made whether the current mode is the play mode in the state 384. If the answer to the state 384 is YES, a determination may be made as to whether a sound is being played in a state 386. If the answer to the state 386 is YES, the play icon 56 (FIG. 2D) may flash in a state 388. Subsequently, the process may proceed to the state 416. If the answer to the state 386 is NO, the play icon 56 may be highlighted in a state 390. Then, the process may proceed to the state 416. If the answer to the state 384 is NO, the process may proceed to a state 392.

In the state 392, a determination is made whether the current mode is the record mode. If the answer to the state 392 is YES, a determination may be made as to whether a sound is being recorded in a state 394. If the answer to the state 394 is YES, the process may proceed to a state 398. In the state 398, the record icon 58 may flash. Then, the process may proceed to the state 416. If the answer to the state 394 is NO, the record icon 58 may be highlighted in a state 402. Subsequently, the process may proceed to the state 416. If the answer to the state 392 is NO, the process may proceed to a state 404.

In the state 404, a determination is made whether the current mode is the SetWeeks submode. If the answer to the state 404 is YES, the Weeks Pregnant of the week-and-day counter 30 flash in a state 406. Also, the Setup icon may be turned on in the state 406. Then, the process may proceed to the state 416. If the answer to the state 404 is NO, the process may proceed to a state 408.

In the state 408, a determination is made whether the current mode is the SetDays submode. If the answer to the state 408 is YES, the DueDays of the week-and-day counter 30 may flash in a state 410. Also, the Setup icon may be turned on in the state 410. Then, the process may proceed to the state 416. If the answer to the state 408 is NO, the process may proceed to a state 412.

In the state 412, a determination is made whether the current mode is the SetLanguage submode. If the answer to the state 412 is YES, the word "days to go" of the day counter 30 may flash in the current language in a state 414. Also, the Setup icon may be turned on in the state 414. Then, the process may proceed to the state 416. If the answer to the state 412 is NO, the process may proceed to the state 416. In the state 416, the process for every 0.1 second started in the state 302 in FIG. 5A may exit.

Figure 6:
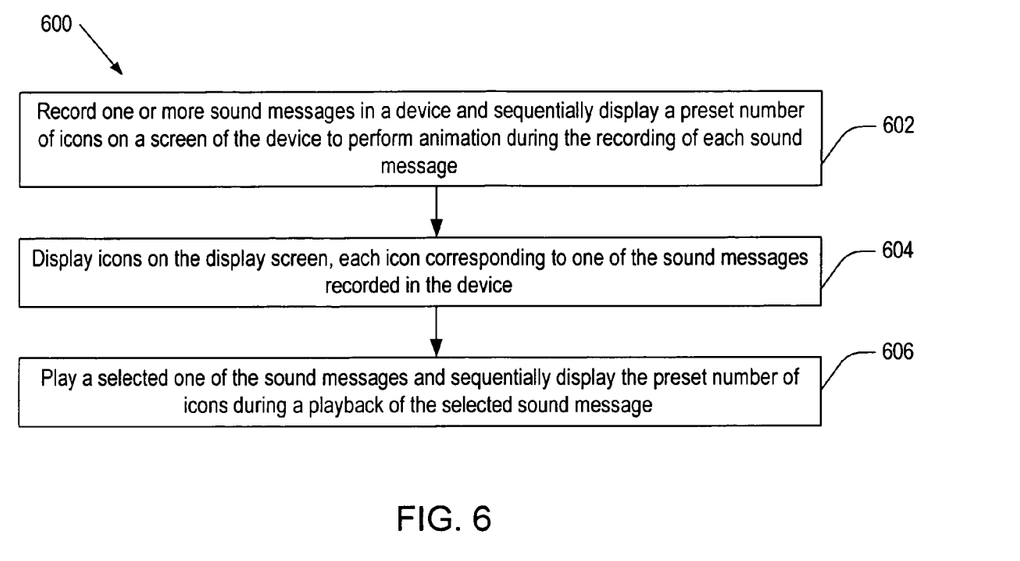
FIG. 6 shows a flow chart illustrating the steps that may be carried out to record and play sound recordings using the device depicted in FIG. 1A according to the present invention.

FIG. 6 is a flow chart shown at 600 illustrating the steps that may be carried out to record and play sound recordings using the device 10 according to the present invention. In a state 602, the user of the device 10 may record one or more sound messages by pressing down the EVENT button 12 in the record mode. During the recording of each sound recording, a preset number of footprints 28 may be sequentially displayed on the screen, more specifically, on the record count window 18 to perform an animation. Then, in a state 604, one or more of the footprints 28 are displayed on the record count window 18, wherein each footprint 28 corresponds to one of the sound messages recorded in the device. The user is able to count the number of sound messages recorded in the device by counting the footprints 28 displayed on the screen. In a state 606, the user may select and play one of the sound messages in a state 606. During a playback of the selected sound message, the record count window 18 may sequentially display the preset number of the icons to perform an animation.

In an alternative embodiment of the present invention, the device 10 may store and display visual images as well as audio recordings. The visual image may be received through the computer communication Input/Output 78 (FIG. 3). The device 10 may also include a visual image controller and a miniature camera to capture still images or video images. Hereinafter, the term "visual image" collectively refers to both still and video images. The visual image controller may control the miniature camera to capture visual images and send visual images to the LCD screen 18 for display. The received/captured visual image may be stored in a storage device, such as the data memory storage 94 and the flash memory 91. The visual image controller may be operated via the EVENT button 12 and MODE button 12 in the same manner as the Record/Playback controller 88 is operated, i.e., a visual image may be displayed and recorded by performing processes similar to those illustrated in FIGS. 4A-5C. For instance, as in the state 224, a visual image may be recorded by the miniature camera of the device when the device is in a record mode and EVENT button 12 has been pressed more than ½ seconds. In another alternative embodiment, a visual image and a sound recording may be recorded and played simultaneously. In this embodiment, when the device plays a sound recording, the play icon 56 may blink and the corresponding visual image may be displayed on the LCD screen 18. For the purpose of simplicity, the detailed description of processes for capturing and displaying visual images is not given in the present application. However, one of ordinary skill in the art would easily appreciate that processes similar to those illustrated in FIGS. 4A-5C can be performed to operate the device in the context of visual images.

It should be understood, of course, that the foregoing relates to exemplary embodiments of the invention and that modifications may be made without departing from the spirit and scope of the invention as set forth in the following claims.

What is claimed is:

1. A device for tracking pregnancy progress, comprising:
an input member actuatable by a user to record one or more sound recordings in the device;
an audio member for playing the sound recordings recorded in the device; and
a display screen for displaying icons and pregnancy progress data, each icon corresponding to one of the sound recordings so that the user of the device is able to count the number of sound recordings recorded in the device by counting the icons,
wherein each of the icons is in the form of a footprint and wherein said display screen sequentially displays said icons to perform an animation during playback and recording of each said sound recording.

2. A device as recited in claim 1, further comprising:
a data storage for storing the sound recordings;
wherein the user actuates the input member to scroll down through the sound recordings recorded in said data storage.

3. A device as recited in claim 2, further comprising:
a Doppler instrument for picking up a fetal heartbeat sound and recording the heartbeat sound into said data storage.

4. A device as recited in claim 2, wherein said audio member receives a sound and communicates the sound to said data storage, said audio member being operable as a speaker.

5. A device as recited in claim 4, wherein the sound is one selected from the group consisting of heartbeat sound from a Doppler instrument, baby's first cry and baby's first words.

6. A device as recited in claim 1, further comprising a voice recognizer coupled to said audio member and operable to recognize the user's voice command.

7. A device as recited in claim 1, further comprising a global positioning system for determining the user's current location and providing a navigational guidance for the user.

8. A device as recited in claim 1, further comprising a processor, wherein the pregnancy progress data includes an indication of pregnancy period from inception in weeks and days, wherein said processor calculates a countdown of days-to-go using the pregnancy progress data, and wherein said display screen displays the countdown if the countdown is less than a predetermined number.

9. A device as recited in claim 1, wherein said display screen has multiple language settings.

10. A device as recited in claim 1, wherein said display screen displays a digital image of a baby's ultrasound scan.

11. A device as recited in claim 1, further comprising an Input/Output for communicating with an electronic device.

12. A device as recited in claim 11, wherein the electronic device is one selected from the group consisting of a computer and a personal digital assistant (PDA).

13. A device as recited in claim 11, wherein the Input/Output is a wireless device.

14. A device as recited in claim 1, further comprising a flash memory for storing one or more audio instructions for use of the device.

15. A device as recited in claim 1, further comprising:
a camera for capturing visual images; and
a visual image controller for controlling said camera to capture the visual images and displaying the visual images on the display screen.

16. A method for storing and playing sound recordings using a device that includes a display screen, comprising:
causing the device to record one or more sound recordings in the device;
causing the device to display icons in the form of a footprint on the display screen, each of the icons corresponding to one of the sound recordings recorded in the device so that the user of the device is able to count the sound recordings by counting the icons;
causing the device to play the sound recordings; and
causing the device to sequentially display the icons during recording or playback of each of the sound recordings thereby to perform an animation on said display screen.

17. A method as recited in claim 16, further comprising:
recording a heartbeat sound into a data storage of the device; and
causing the device to play the heartbeat sound.

18. A method as recited in claim 16, wherein each of the icons is in the form of a footprint.

19. A method as recited in claim 16, wherein said device further includes a voice recognizer, further comprising:
causing the voice recognizer to recognize the user's voice command.

20. A method as recited in claim 16, further comprising:
providing one or more verbal instructions for use of the device.

21. A method as recited in claim 16, further comprising:
causing the device to record one or more visual images in the device; and
causing the device to display the visual images on the display screen.

* * * * *